United States Patent
Styrc (10) Patent No.: US 8,202,309 B2
(45) Date of Patent: Jun. 19, 2012

(54) KIT FOR INSERTING A CAVITY-TREATMENT ELEMENT AND METHOD FOR PREPARING AN ASSOCIATED TREATMENT ELEMENT

(75) Inventor: Mikolaj Witold Styrc, Kopstal (LU)

(73) Assignee: Laboratoires Perouse, Ivry le Temple (FR)

( * ) Notice: Subject to any disclaimer, the term of this patent is extended or adjusted under 35 U.S.C. 154(b) by 604 days.

(21) Appl. No.: 11/920,628

(22) PCT Filed: May 15, 2006

(86) PCT No.: PCT/FR2006/001088
§ 371 (c)(1),
(2), (4) Date: Jun. 23, 2009

(87) PCT Pub. No.: WO2006/123046
PCT Pub. Date: Nov. 23, 2006

(65) Prior Publication Data
US 2009/0299449 A1    Dec. 3, 2009

(30) Foreign Application Priority Data
May 19, 2005   (FR) ...................... 05 05044

(51) Int. Cl.
*A61F 2/06* (2006.01)
(52) U.S. Cl. ................................... 623/1.11
(58) Field of Classification Search ........ 623/1.11–1.12, 623/1.23; 606/108
See application file for complete search history.

(56) References Cited

U.S. PATENT DOCUMENTS

| | | | | |
|---|---|---|---|---|
| 4,271,839 | A | * | 6/1981 | Fogarty et al. ................ 606/194 |
| 4,863,440 | A | * | 9/1989 | Chin ............................ 604/271 |

(Continued)

FOREIGN PATENT DOCUMENTS

EP    0 472 731    3/1992

(Continued)

OTHER PUBLICATIONS

International Search Report issued Oct. 4, 2006 in the International (PCT) Application of which the present application is the U.S. National Stage.

*Primary Examiner* — Gary Jackson
*Assistant Examiner* — Amy Shipley
(74) *Attorney, Agent, or Firm* — Wenderoth, Lind & Ponack, L.L.P.

(57) ABSTRACT

A kit includes an implantable treatment element (13) which can be radially deformed between a retracted state and a deployed state, and a sheath (15) for maintaining the treatment element (13) in its retracted state. The kit also includes a member (19) for pulling the treatment element (13) into the sheath (15), which includes a sleeve (17) for receiving the treatment element (13) which can slide in relation to the sheath (15) between an expanded position for receiving the treatment element (13) and a compressed interposed position between the treatment element (13) and the sheath (15). The treatment element (13) is substantially axially fixed in relation to the receiving sleeve (17) when the sleeve (17) moves between its receiving and interposed positions. The kit can be used to insert endoprostheses into a blood vessel.

12 Claims, 5 Drawing Sheets

U.S. PATENT DOCUMENTS

| | | | |
|---|---|---|---|
| 5,364,345 A * | 11/1994 | Lowery et al. | 604/500 |
| 5,662,703 A | 9/1997 | Yurek et al. | |
| 6,059,813 A | 5/2000 | Vrba et al. | |
| 6,238,410 B1 | 5/2001 | Vrba et al. | |
| 6,395,014 B1 * | 5/2002 | Macoviak et al. | 606/200 |
| 7,285,130 B2 * | 10/2007 | Austin | 623/1.12 |
| 7,393,358 B2 * | 7/2008 | Malewicz | 623/1.11 |
| 7,955,370 B2 * | 6/2011 | Gunderson | 623/1.11 |
| 2002/0077691 A1 | 6/2002 | Nachtigall | |
| 2007/0016247 A1 * | 1/2007 | Euteneuer et al. | 606/200 |
| 2008/0027528 A1 * | 1/2008 | Jagger et al. | 623/1.11 |

FOREIGN PATENT DOCUMENTS

| | | |
|---|---|---|
| WO | 96/32078 | 10/1996 |
| WO | 00/27309 | 5/2000 |
| WO | 02/49538 | 6/2002 |

* cited by examiner

KIT FOR INSERTING A CAVITY-TREATMENT ELEMENT AND METHOD FOR PREPARING AN ASSOCIATED TREATMENT ELEMENT

BACKGROUND OF THE INVENTION

1. Field of the Invention

The present invention relates to a kit for treating a blood circulation system, comprising:

at least one implantable treatment element which can be radially deformed between a retracted state and a deployed state;

a sheath for holding the treatment element in its retracted state;

means for pulling the treatment element into the sheath;

The kit is used in particular for inserting endoprosthesis into a blood vessel.

2. Description of Related Art

Such a kit is disclosed in publication EP 0 472 731, in which an endoprosthesis in a deployed state is introduced into a sheath for maintaining said endoprosthesis in a retracted state.

The means for introducing the endoprosthesis into the sheath comprise a pull-wire at one end of the endoprosthesis and a funnel mounted to the end of the sheath which allows the endoprosthesis to contract when it is pulled inside the sheath by the string.

A device of this type is not entirely satisfactory. In fact, the wire must be pulled very firmly in order to pull the endoprosthesis into its sheath. The endoprosthesis must therefore be inserted into its sheath before the kit is packaged and not during a surgical operation just before the endoprosthesis is implanted.

An object of the invention is therefore to provide a kit for treatment of a blood circulation system in which a treatment element can be easily inserted, in particular during a surgical operation, into a sheath for maintaining said element in a retracted position. Furthermore, the kit must allow the treatment element to be easily extracted when it is implanted, thus limiting the risk of injuring the patient.

SUMMARY OF THE INVENTION

To this end, the invention relates to a treatment kit of the aforementioned type, characterised in that the introduction means comprise at least one sleeve for receiving the treatment element, which can slide in relation to the sheath between an expanded position for receiving the treatment element outside the sheath and a compressed interposed position between the treatment element and the sheath, the treatment element being substantially axially fixed in relation to the receiving sleeve when the receiving sleeve moves between its receiving and interposed positions, and in that the sleeve comprises at least one return strand curved back to the outside of the sheath, the introduction means comprising an element for pulling the curved strand, or each curved strand towards a proximal end of the sheath, the pulling element being able to slide along the sheath when the sleeve is displaced from its receiving position to its interposed position.

The kit according to the invention may comprise one or more of the following features taken in isolation or in any technically feasible combination:

the receiving sleeve comprises a region for retaining an end of the treatment element and a region for guiding the treatment element when the retaining region is inside the sheath and the guiding region projects outside the sheath;

the treatment element is detachably fixed to the introduction means;

the introduction means form the means for extracting the treatment element from the sheath;

the receiving sleeve comprises at least two flexible prongs joined together by a common base and having free ends which are not connected;

the introduction means comprise an element for controlling displacement of the receiving sleeve in relation to the sheath, the controlling element and the receiving sleeve being integral;

the coefficient of friction between the receiving sleeve and the sheath is less than the coefficient of friction between the treatment element and the sheath;

the treatment element is an endoprosthesis comprising a deployable frame; and the treatment element is a deployable valve;

the sleeve comprises, in its receiving position, an end for retaining the endoprosthesis, the pulling element being integral with a free end of the sleeve;

the pulling element comprises a collar slidingly mounted to the outside of the sheath;

the pulling element is connected in translation to the retaining end;

the pulling element is disposed in the sheath, the sheath comprising at least one lateral passage in which the free end of the sleeve is engaged; and each flexible prong is curved around a distal region of the sheath delimited by a lateral passage and a distal end of the sheath.

BRIEF DESCRIPTION OF THE DRAWINGS

The invention will be better understood after reading the description which follows, given solely by way of example and with reference to the attached drawings, in which.

DETAILED DESCRIPTION OF THE INVENTION

Figure 1:
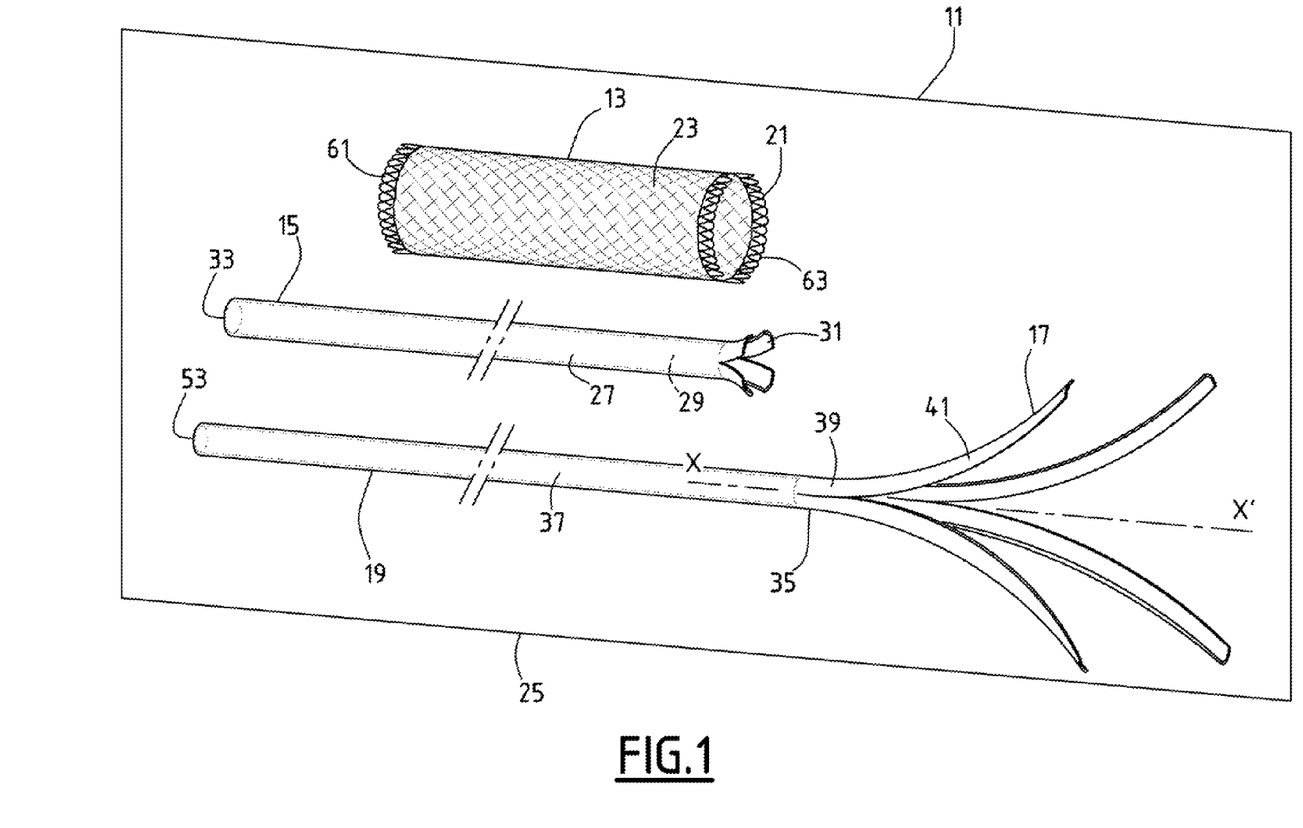
FIG. 1 is an elevation of a first packaged kit, for which a protection is not sought.

The treatment kit 11 illustrated in FIG. 1, which is not covered by the claims of this application, comprises a tubular endoprosthesis 13, which can be deployed between a retracted state and a deployed state, a sheath 15 for maintaining the endoprosthesis 13 in its retracted state and means 19 for inserting the endoprosthesis 13 into the sheath 15 which comprise a sleeve 17 for receiving the endoprosthesis 13.

The endoprosthesis 13 comprises a tubular wire-mesh 21 made of a metal which can be implanted, such as stainless steel, which has resilient properties. Thus, in the example illustrated, the endoprosthesis 13 is self-expanding.

As is known per se, the endoprosthesis 13 can spontaneously deform from its retracted state, in which it has a small diameter, to its deployed state, in which it has a greater diameter, said deployed state being its rest state.

In the illustrated example, the wire-mesh 21 of the endoprosthesis is embedded in an expandable film 23, such as an elastomer, which is impervious to liquids. This elastomer could be, for example, a silicone.

An endoprosthesis of this type is generally denoted by the term "stent".

The elements of the treatment kit 11 are packaged in the same packaging 25 formed of, for example, an airtight and watertight pocket. The endoprosthesis 13 is retained in its deployed state in said packaging 25.

The sheath 15 is formed of a tube 27 made of plastics material, for example, polytetrafluoroethylene (PTFE), delimiting an inner tube 29 which has a diameter substantially equal to the diameter of a transverse section of the endoprosthesis 13 in its retracted position.

The sheath 15 extends longitudinally between a distal end 31 for insertion into a blood vessel and a proximal end 33 for surgical access. The end 31 has a divergent conical shape at its tip. However, in a variation, the end 31 is straight.

In the example illustrated by FIG. 1, the means 19 for introducing the endoprosthesis 13 into the sheath 15 are formed from a resilient tube 35 made of polytetrafluoroethylene (PTFE) in which there are arranged a plurality of longitudinal slits from the distal end of said tube 35.

The tube 35 delimits, in its slitted part, the receiving sleeve 17 and, in its solid part, a cylinder 37 for controlling the movement of the endoprosthesis.

The receiving sleeve 17 of the endoprosthesis 13 comprises a ring 39 for retaining an end of the endoprosthesis 13 and a plurality of flexible guiding prongs 41.

The retaining ring 39 is formed by the end of the solid part of the tube 35. It has an outer diameter which is smaller than or substantially equal to the inner diameter of the sheath 15.

The flexible prongs 41 extend from the retaining ring 39 to the free ends which are not connected.

The prongs 41 are laterally delimited by the slits arranged in the tube 39.

The flexible prongs 41 are displaceable between a position at a distance from a central axis X-X' defined by the ring 39 and a position next to said central axis X-X'.

The length of the flexible prongs 41 is at least substantially equal to the length of the endoprosthesis 13 in such a way that when an end of the endoprosthesis 13 is inserted into the ring 39, the prongs 41, in their position in the proximity of axis X-X', extend in a manner substantially following the length of the endoprosthesis 13.

The receiving sleeve 17 can slide in relation to the sheath 15 between a dilated position for receiving the endoprosthesis 13 outside the sheath 15, in which the prongs 41 are disposed at a distance from the central axis X-X', an intermediate position for inserting the ring 39 into the sheath 15 and a compressed interposed position in the sheath 15 between the endoprosthesis 13 and the sheath 15.

Figure 2:
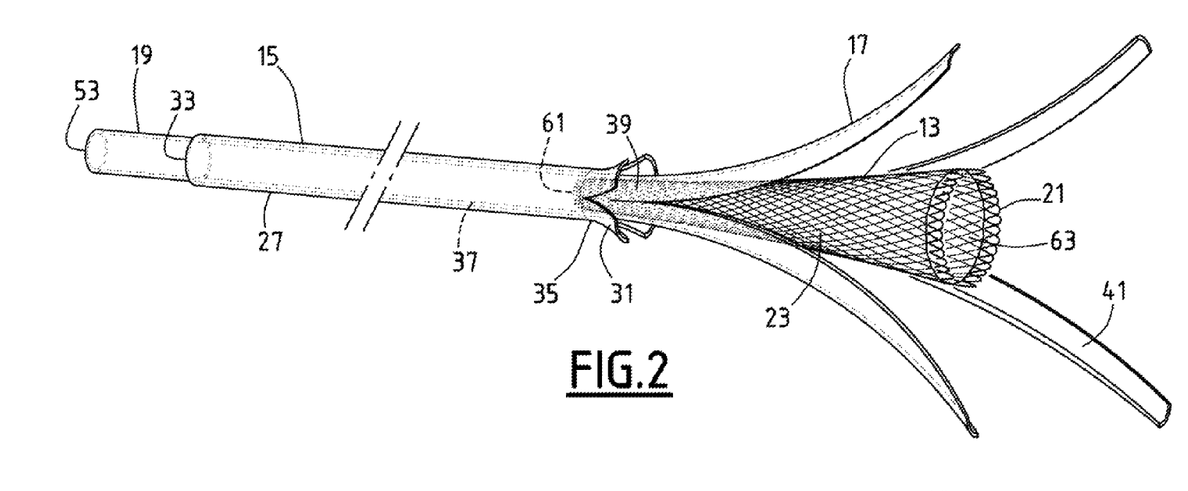
FIG. 2 is an elevation of the kit in a first position of the receiving sleeve.

In the intermediate position of insertion, illustrated by FIG. 2, the retaining ring 39 is inserted into the sheath 15. The prongs 41 project at least partially outside the sheath 15 and have a shape which diverges substantially towards the outside of the sheath 15. The prongs 41 are progressively compressed towards the axis X-X' by being pressed against the peripheral region at the distal end 31 of the sheath 15.

Figure 3:
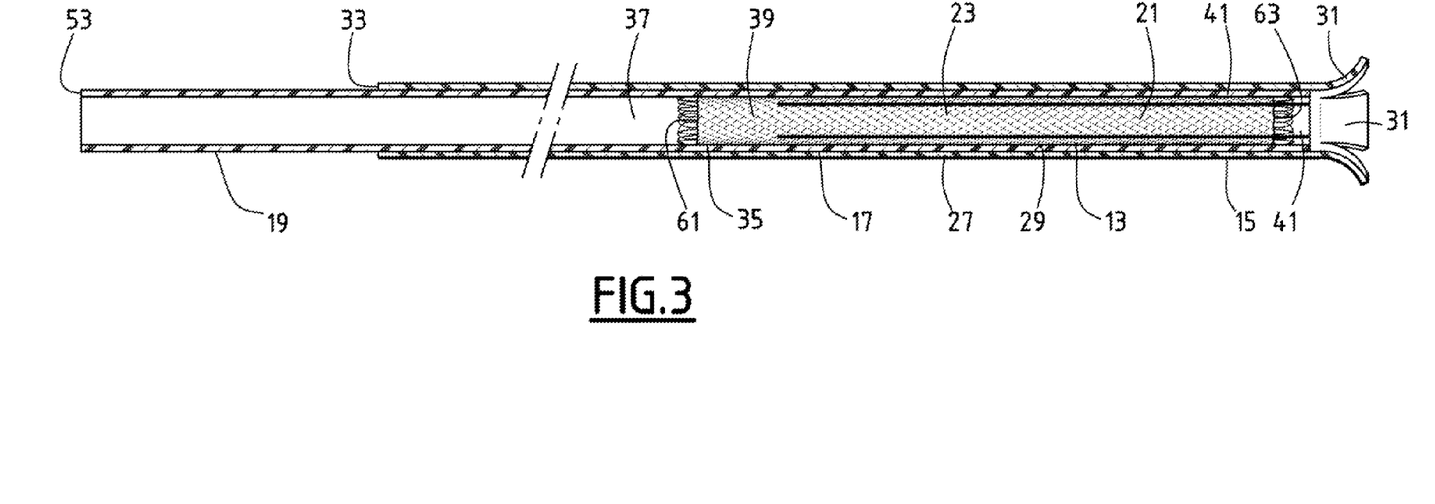
FIG. 3 is a cross-section along a median plane of the kit in a second position of the receiving sleeve.

In the interposed position, illustrated by FIG. 3, the sleeve 17 containing the endoprosthesis 13 is substantially completely inserted inside the sheath 15. The endoprosthesis 13 is maintained in its retracted state and the prongs 41 are flattened against the wire-mesh 21 of the endoprosthesis 13 by the internal wall of the sheath 15.

The controlling cylinder 37 is longer than the sheath 15 in such a way that its proximal end 53 protrudes beyond the proximal end 33 of the sheath 15 when it is disposed in the sheath 15.

The controlling cylinder 37 can slide inside the sheath 15 when pushed at its proximal end 53. The controlling cylinder 37 thus also forms a means for extracting the endoprosthesis 13 from the sheath 15 during its implantation in a blood vessel, as described in more detail below.

In the illustrated example, the retaining ring 39, the flexible prongs 41, and the controlling cylinder 37 are integral. In a variation they are separate parts.

As an example, a method for preparing the endoprosthesis 13 for implantation in a blood vessel, from the kit 11, according to the invention will now be described.

This method comprises a preservation phase and a preparation phase.

During the preservation phase, the endoprosthesis 13 is retained in the packaging 25 in its deployed state which allows the mechanical or morphological properties of the endoprosthesis 13 to be preserved, in particular when its tubular wire-mesh 21 is imbedded in a film 23 which is expandable and air and water tight.

In the preservation phase itself, which takes place just before implantation of the endoprosthesis 13 during a surgical operation, the surgeon opens the packaging 25 and cuts the endoprosthesis 13 lengthwise so that it matches the morphology of the blood vessel in which it is to be implanted.

Initially, the surgeon slides the controlling cylinder 37 into the sheath 15. The sleeve 17 is disposed in its position for receiving the endoprosthesis 13, in which the ring 39 and the prongs 41 of the receiving sleeve 17 project outside the sheath 15.

The surgeon then inserts an end 61 of the endoprosthesis 13 into the ring 39 of the sleeve 17, for example by pinching said end 61.

The endoprosthesis 13 is then held in the ring 39 in a tight-fitting manner at the end of the controlling cylinder 37. The prongs 41 face the frame 21.

With reference to FIG. 2, the surgeon then pulls on the proximal end 53 of the controlling cylinder 37 and moves said end 53 away from the sheath 15. The ring 39, the prongs 41 and the endoprosthesis 13 thus slide into the sheath 15.

During said displacement, the prongs 41 slide against the internal wall of the sheath 15 and prevent substantially all contact between said internal wall and the frame 21 of the endoprosthesis 13. Due to the shape of the prongs 41 which diverge towards the exterior of the sheath 15, the prongs 41 are progressively compressed towards the axis X-X' by pressure on the peripheral region at the distal end 31 of the sheath 15. This allows the endoprosthesis 13 to be progressively compressed from its deployed state to its retracted state, as illustrated by FIG. 3.

The presence of the receiving sleeve 17 when the endoprosthesis 13 is inserted into the sheath 15 substantially reduces the frictional force between the endoprosthesis 13 and the inner wall of the sheath 15. The minimum traction that must be applied to the controlling cylinder 37 in order to insert the endoprosthesis 13 into the sheath 15 is thus substantially equal to the friction between the receiving sleeve 17 and the inner wall of the sheath 15.

The ratio of the coefficient of friction between the endoprosthesis 13 and the inner wall of the sheath 15 and to the coefficient of friction between the receiving sleeve 17 and the inner wall of the sheath 15 is greater than 10 and is, in particular, between 10 and 100.

Thus, the traction to be applied to the introduction means 19 is considerably reduced and the endoprosthesis 13 can be inserted into the sheath 15 very easily.

In order to deploy the endoprosthesis 13 into the blood vessel, the surgeon implants a surgical guide (not illustrated) into the blood vessel or the vein and this runs from the external insertion point to the region of the vein or the artery where the endoprosthesis 13 is to be implanted.

The endoprosthesis 13 is maintained in its retracted position by the sheath 15 and is then inserted up to the point where it is to be implanted by means of displacement along the surgical guide.

Once the endoprosthesis 13 has been inserted, the surgeon deploys the distal end 63 of the endoprosthesis 13 into the vessel by pushing the controlling cylinder 37 in order to displace its proximal end 53 towards the sheath 15.

The distal end 63 of the endoprosthesis 13 opens out outside the sheath by spreading open the flexible prongs 41 in such a way that the wire-mesh 21 moves close to the walls of the vessels to be treated and comes to press on said walls.

When the endoprosthesis 13 is extracted from the sheath 15, the presence of the receiving sleeve 17 also substantially eliminates the friction between the endoprosthesis 13 and the sheath 15 which facilitates deployment of the endoprosthesis 13 into the vessel.

Once the distal end 63 of the endoprosthesis 13 has been settled against the walls of the vessel to be treated the surgeon proceeds with removing the sleeve 17 and the sheath 15 from the blood vessel.

Figure 4:
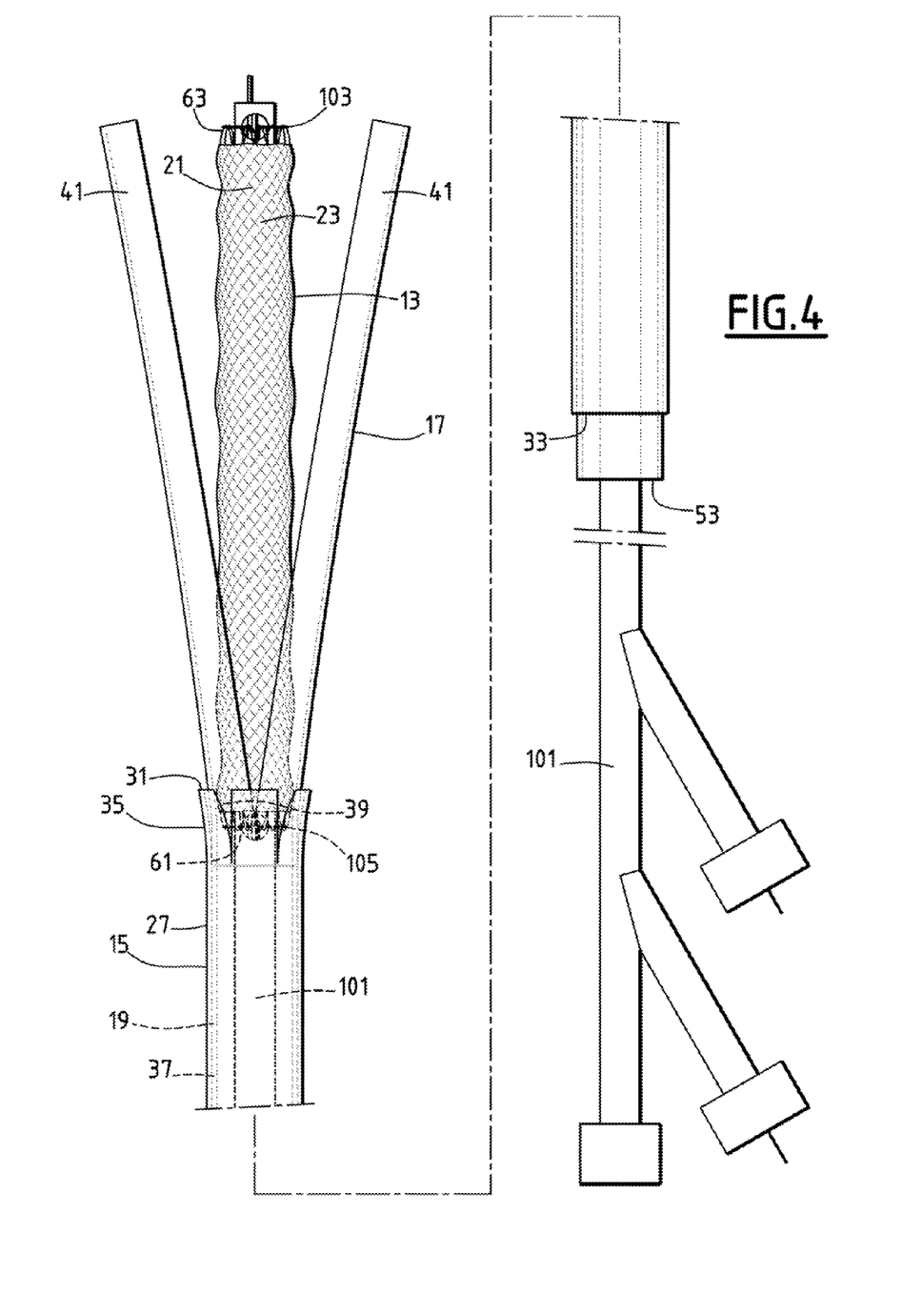
FIG. 4 is a view, similar to that of FIG. 2, of a second treatment kit for which no protection is sought.

In the variant illustrated in FIG. 4, the endoprosthesis 13 is mounted coaxially on a sole prop 101 and is fixed on said prop 101 by detachable retaining filaments 103, 105 of the type described in the French application No. 03 14424.

The filaments 103, 105 are engaged in the frame 21 respectively at the distal end 63 and proximal end 61 of the endoprosthesis 13 and form at these ends 61, 63 tightening loops, the length of which can be controlled by extensions of the filaments 103, 105 up to the proximal end of the prop 101.

The diameter of the prop 101 is substantially smaller than the inner diameter of the sheath 15 and of the ring 39.

Thus, during the preservation phase, the receiving sleeve 17, the controlling cylinder 37 engaged in the sheath 15 and the endoprosthesis 13 in its deployed state are coaxially disposed on the prop 101.

As disclosed in the cited French application, during surgery the surgeon starts by gripping the tightening loops at the ends of the wire-mesh 121 by pulling the extensions of the wires 103, 105 before bringing the endoprosthesis 13 into an intermediate retracted state.

Next, in order to insert the endoprosthesis 13 into the sheath 15, the surgeon introduces the proximal end 61 of the endoprosthesis into the ring 39 then simultaneously displaces the proximal ends of the prop 101 and the controlling cylinder 37 away from the proximal end 33 of the sheath 15.

The endoprosthesis 13 received in the sleeve 17 then penetrates the sheath 15 as previously described.

Once inside the sheath 15, the endoprosthesis 13 has a cross-section with a minimal diameter along the whole of its length.

Its deployment into the blood vessel takes place as in the cited French application.

Figure 5:
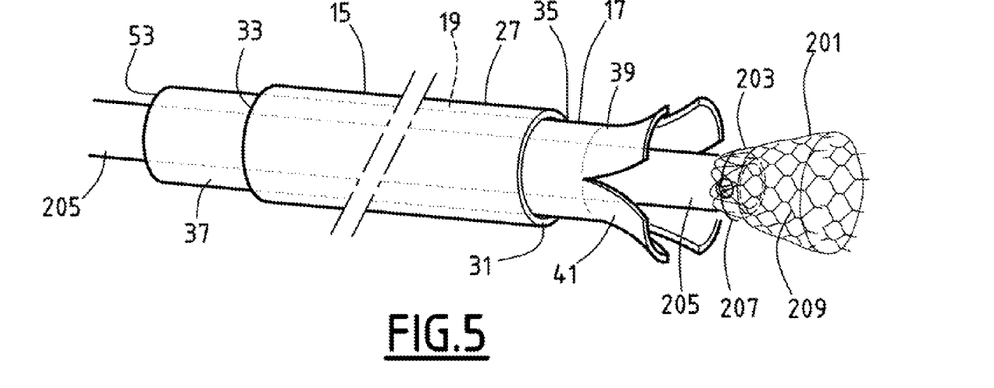
FIG. 5 is an elevation of a third treatment kit for which no protection is sought.
Figure 6:
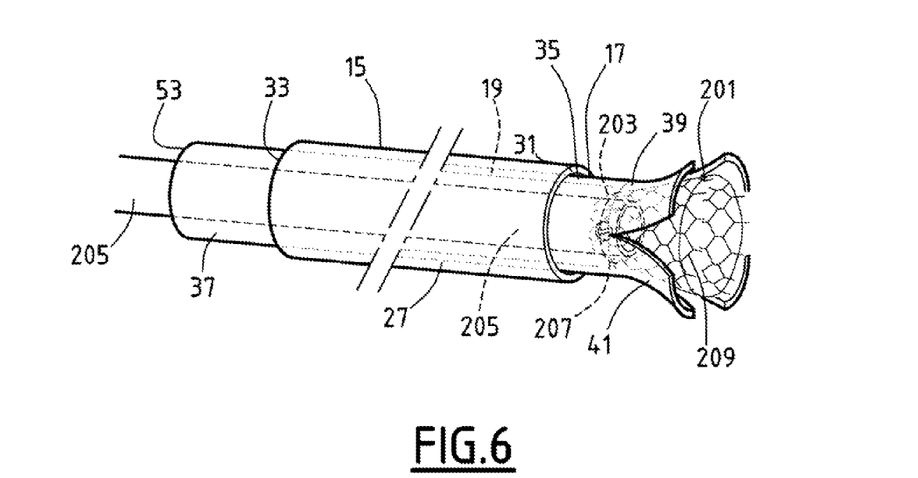
FIG. 6 is a view, similar to that of FIG. 2, of the third treatment kit according to the invention.

In a third variant illustrated in FIGS. 5 and 6, the kit comprises a heart valve 201 deployable between a retracted state and a deployed state.

During the preservation phase, the valve 201 in its deployed state is fixed at its converging end 203 to an introduction tube 205. This fastening takes place, for example, with the aid of a retaining filament 207 which can be detached from the external point of insertion into the blood circulation system to be treated.

Unlike the first kit, the receiving sleeve 17 then the sheath 15 are coaxially mounted on the introduction tube 205 in such a way that the proximal end of said tube 205 projects beyond the sheath 15.

In order to prepare the valve 201 for implantation, the surgeon slides the proximal end of the tube 205 at a distance from the proximal end 33 of the sheath 15 into the sheath 15 whilst keeping the receiving sleeve 17 substantially fixed in relation to the sheath 15 with the aid of the controlling cylinder 37.

Displacement of the tube 205 allows the converging end 203 of the valve 201 to be introduced into the ring 39. In this intermediate position, illustrated by FIG. 6, the flexible prongs 41 face the wire-mesh 209 of the valve 201 and thus have a shape which diverges substantially away from the sheath.

The surgeon then displaces the proximal end 53 of the controlling cylinder 37 away from the sheath 15. The valve 201 being fixed in the ring 39, the displacement of the proximal end of the tube 205 at a distance from the sheath 15 continues. The assembly formed by the valve 201 and its receiving sleeve 17 is then inserted into the sheath 15.

Deployment of the valve 201 takes place as previously described for the endoprosthesis 13, the last step consisting of detaching the retaining wire 207 from the valve 201 then removing the tube 205 from the blood circulation system.

It is therefore possible to provide a kit for treating a blood circulation system which allows simple insertion, requiring only a gentle pull, of a treatment element 13, 201 into a sheath 15 for maintaining said element 13, 201 in a retracted position. This insertion can take place easily during surgery.

Furthermore, the kit facilitates extraction of the treatment element 13, 201 from the sheath 15 during the implantation of said element in a blood circulation system.

This kit allows the treatment element 13, 201 to retain its deployed state and, if necessary, to be cut to size just before its implantation so as to match the length of the blood vessel in which it is to be implanted.

Figure 7:
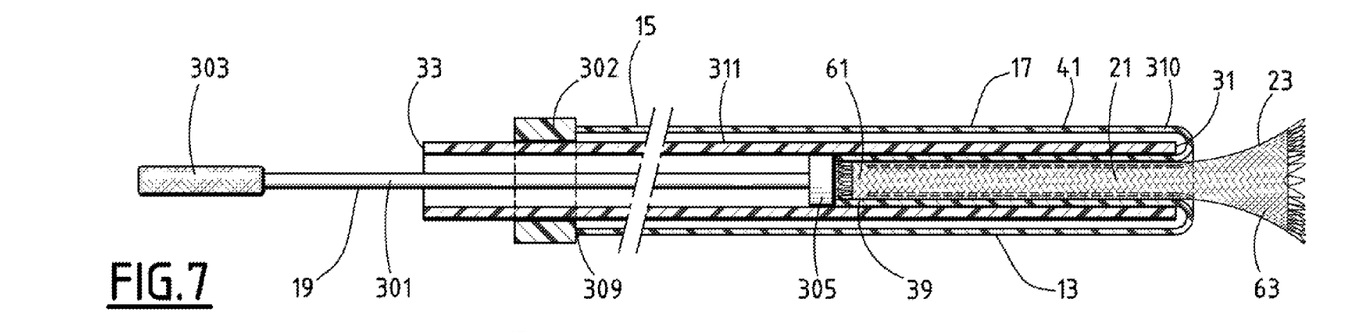
FIG. 7 is a view, similar to that of FIG. 3, of a first treatment kit according to the invention.

The first kit according to the invention, illustrated in FIG. 7, differs from the kit illustrated in FIG. 3 with regard to the following characteristics.

The introduction means 19 (i.e., a pulling unit) of the endoprosthesis 13 into the sheath 15 comprise a rod 301 for controlling displacement of the receiving sleeve 17 engaged in the sheath 15 and a pulling collar 302 of the sleeve 17 mounted on the sheath 15.

The rod 301 is equipped, at its proximal end, with a grip 303, and at its distal end, with a piston 305 for pushing the endoprosthesis 13.

The piston 305 is slidingly mounted inside the sheath 15.

The retaining ring 39 of the endoprosthesis 13 formed in the receiving sleeve 17 is fixed on a distal surface of the piston 305, opposite the rod 301.

Each prong 41 of the sleeve 17 comprises a return strand 310 which projects outside the sheath 15. The return strands 310 are curved back against the outer surface, denoted as 311, of the sheath.

The free ends 309 of the prongs 41, arranged opposite the retaining ring 39, are fixed along a distal peripheral surface of the pulling collar 302.

The collar 302 is slidingly mounted on an outer surface 311 of the sheath 15. It is mobile along the sheath 15 between a proximal position of deployment of the endoprosthesis 13 into the sheath 15, in which the collar is at a distance from the detached end of the endoprosthesis, and a distal position which it is in when the endoprosthesis 13 is completely inserted into the sheath 15 and in which the collar is nearer to the releasing end.

The collar 302 further comprises guiding means (not illustrated) which prevent the collar from rotating about the longitudinal axis of the sheath 15.

The length of the prongs 41 is at least three times greater than the length of the endoprosthesis 13 in such a way that the collar 302, in its proximal and distal positions, remains outside the patient's body. As for the rest, the features of the first kit according to the invention are similar to the features of the first kit described in FIGS. 1 to 3.

Initially, in order to insert the endoprosthesis 21 into the sheath 15, the piston 305 is disposed in the proximity of the distal end 31 of the sheath. The retaining ring 39 is thus arranged in the sheath 15 in the proximity of the distal end 31. The collar 302 is maintained in its proximal position. The position of the collar 302 is adjusted manually by pulling it towards the proximal end 33 of the sheath 15 so the return strands 310 of the prongs 41 are flattened on the outer surface 311 of the sheath. The maximal transverse dimension of the kit is therefore reduced.

Next, the proximal end 61 of the endoprosthesis 13 is inserted into the retaining ring 39. The piston 305 is thus displaced towards the proximal end 33 of the sheath 15 by using the grip 303.

At the time of this displacement, the prongs 41 and the endoprosthesis 13 penetrate the sheath 15. The prongs 41 interpose between the endoprosthesis 13 and the sheath 15. Furthermore, the collar 302 is pulled towards its distal position by the guiding prongs 41.

In order to deposit the endoprosthesis 13 inside the patient, the surgeon simultaneously moves the grip 303 towards the distal end 31 of the sheath 15 and the collar 302 towards the proximal end 33 of said sheath 15 to pull the return strands 310 of the prongs 41 towards the end 33.

Thus, the prongs 41 are flattened against the outer surface 311 of the sheath 15, which limits the risk of injuring the patient during deployment of the endoprosthesis, in particular by tearing the wall of the blood vessel.

In another variant, the first kit according to the invention may include the characteristics of the kit in FIG. 4 or of the kit in FIGS. 5 and 6 with the exception of the flexible prongs 41 which are curved back to the outside of the sheath.

Figure 8:
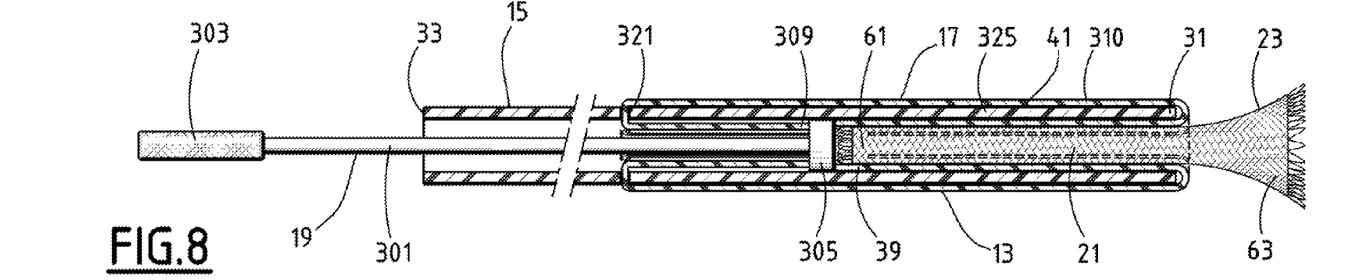
FIG. 8 is a view, similar to that of FIG. 3, of a second treatment kit according to the invention.

The second kit according to the invention, illustrated in FIG. 8, differs from the kit illustrated in FIG. 7 with regard to the following characteristics.

Figure 9:
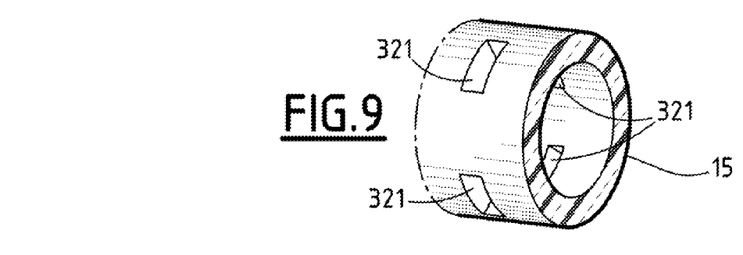
FIG. 9 is a partial perspective view of the sheath of the second kit according to the invention illustrated in FIG. 8.

As illustrated in FIG. 9, the sheath 15 comprises a plurality of transverse passages 321 arranged in the lateral wall of the sheath. These passages 321 extend substantially along the periphery of a transverse section of the sheath 15. The distance between the distal end 31 and the passages 321 is greater than the length of the endoprosthesis 13.

The number of passages 321 is equal to the number of prongs 41. Furthermore, the width of the passages 321, taken from along the periphery, is substantially equal to the width of the prongs 41.

The free ends 309 of prongs 41 are engaged through the passages 321 and are fixed on a proximal surface of the piston 305.

The piston thus forms a means for pulling the return strands 310.

The length of the prongs 41 is designed to be substantially equal to two times the length which separates the proximal end 31 of the passages 321. The return strands 310 of the prongs 41 arranged outside the sheath 15 are therefore flattened on the outer surface 310 of the sheath 15.

Each prong 41 is curved around a distal region 325 of the sheath 15 delimited by a passage 321 and the distal end 31. Each prong 41 forms, around this region, a conveyor band for inserting the endoprosthesis 13 into the sheath 15.

Thus, in order to insert the endoprosthesis 13 into the sheath 15, the ring 39 is placed at the distal end 31 of the sheath 15 by displacement of the piston 305. Then, the proximal end 61 of the endoprosthesis 13 is inserted into the ring 39 and the piston 305 is displaced towards the distal end 33 of the sheath 15.

Deployment of the endoprosthesis 13 takes place by displacing said piston 305 towards the proximal end 31 of the sheath 15.

The invention claimed is:

1. A kit for treating a blood circulation system, comprising:
    at least one implantable treatment element which can be radially deformed between a refracted state and a deployed state;
    a sheath for maintaining the treatment element in its retracted state; and
    a pulling unit for pulling the treatment element into the sheath,
    wherein the pulling unit comprises a sleeve for receiving the treatment element, the sleeve being slidable in relation to the sheath between an expanded position for receiving the treatment element outside the sheath and a compressed interposed position between the treatment element and the sheath, the treatment element being substantially axially fixed in relation to the sleeve when the sleeve moves between its receiving and interposed positions,
    wherein the sleeve includes at least one return strand curved back to the outside of the sheath, and the pulling unit includes a pulling element for pulling the at least one return strand towards a proximal end of the sheath, the pulling element being able to slide along the sheath during displacement of the sleeve between its receiving position and its interposed position,
    wherein the sleeve includes a retaining end for retaining the treatment element in the receiving position of the sleeve, the pulling element being connected to the retaining end of the sleeve so as to be movable together with the retaining end in translation,
    and wherein the pulling element is disposed in the sheath, the sheath comprising at least one lateral passage in which a free end of the sleeve is engaged.

2. The kit according to claim 1, wherein the sleeve comprises a region for retaining an end of the treatment element and a region for guiding the treatment element, the retaining region and the guiding region being configured such that the guiding region projects outside the sheath when the retaining region is inside the sheath.

3. The kit according to claim 1, wherein the treatment element is detachably fixed to the pulling unit.

4. The kit according to claim 1, wherein the pulling unit is configured to extract the treatment element from the sheath.

5. The kit according to claim 1, wherein the sleeve comprises at least two flexible prongs joined together by a common base and having free ends which are not connected.

6. The kit according to claim 5, wherein each flexible prong is curved around a distal region of the sheath, the distal region of the sheath being located between a distal end of the sheath and the at least one lateral passage.

7. The kit according to claim 1, wherein the pulling unit further comprises an element for controlling displacement of the sleeve in relation to the sheath, the controlling element and the sleeve being integral.

8. The kit according to claim 1, wherein a coefficient of friction between the sleeve and the sheath is less than a coefficient of friction between the treatment element and the sheath.

9. The kit according to claim 1, wherein the treatment element is an endoprosthesis comprising a deployable frame.

10. The kit according to claim 1, wherein the treatment element is a deployable valve.

11. The kit according to claim 1, wherein the pulling unit includes a rod for controlling the displacement of the sleeve, the rod being connected to the pulling element and having a grip.

12. The kit according to claim 1, wherein the free end of the sleeve is fixed to a proximal surface of the pulling element.

* * * * *